(12) United States Patent
Despatie

(10) Patent No.: US 11,284,929 B2
(45) Date of Patent: Mar. 29, 2022

(54) FLUID DETECTION ASSEMBLY FOR A MEDICAL DEVICE

(71) Applicant: Cryterion Medical, Inc., Carlsbad, CA (US)

(72) Inventor: Claude Despatie, D.D.O. (CA)

(73) Assignee: Cryterion Medical, Inc., Carlsbad, CA (US)

( * ) Notice: Subject to any disclaimer, the term of this patent is extended or adjusted under 35 U.S.C. 154(b) by 764 days.

(21) Appl. No.: 16/160,315

(22) Filed: Oct. 15, 2018

(65) Prior Publication Data

US 2019/0110828 A1 Apr. 18, 2019

Related U.S. Application Data

(60) Provisional application No. 62/573,030, filed on Oct. 16, 2017.

(51) Int. Cl.
*A61B 18/02* (2006.01)
*A61B 18/00* (2006.01)
(Continued)

(52) U.S. Cl.
CPC .......... *A61B 18/02* (2013.01); *A61B 18/1492* (2013.01); *A61B 2017/00867* (2013.01); *A61B 2018/0022* (2013.01); *A61B 2018/00023* (2013.01); *A61B 2018/00255* (2013.01); *A61B 2018/00351* (2013.01); *A61B 2018/00357* (2013.01);
(Continued)

(58) Field of Classification Search
CPC ................ A61B 18/02; A61B 18/1492; A61B 2018/00023; A61B 2018/0022; A61B 2018/00255; A61B 2018/00351; A61B 2018/00357; A61B 2018/00375; A61B 2018/00577; A61B 2018/00744; A61B 2018/00773; A61B 2018/00863; A61B 2018/00892; A61B 2018/00898; A61B 2018/0212; A61B 2018/0231; A61B 2017/00867; A61B 2218/007;
(Continued)

(56) References Cited

U.S. PATENT DOCUMENTS

2005/0228367 A1 10/2005 Abboud et al.

FOREIGN PATENT DOCUMENTS

EP 1887957 A1 2/2008
WO 2006124177 A1 11/2006

OTHER PUBLICATIONS

International Search Report and Written Opinion issued in PCT/US2018/055876, dated Jan. 25, 2019, 11 pages.

*Primary Examiner* — Khadijeh A Vahdat
(74) *Attorney, Agent, or Firm* — Faegre Drinker Biddle & Reath LLP

(57) ABSTRACT

A fluid detection assembly for detecting fluid contamination within a medical device includes a first pair of detection wires and a controller. The first pair of detection wires includes an input first detection wire and a spaced apart output first detection wire that are in fluid communication with one another. The input first detection wire conducts a first electrical signal and the output first detection wire receives the first electrical signal. The controller receives the first electrical signal from the output first detection wire and determines a first propagation delay. The controller can determine a type of fluid contamination, such as blood or saline, based on the first propagation delay. The fluid detection assembly can include a second pair of detection wires that is spaced apart from the first pair of detection wires.

20 Claims, 6 Drawing Sheets

(51) Int. Cl.
　　　*A61B 17/00*　　　(2006.01)
　　　*A61M 25/00*　　　(2006.01)
　　　*A61B 18/14*　　　(2006.01)
(52) U.S. Cl.
　　　CPC .............. *A61B 2018/00375* (2013.01); *A61B 2018/00577* (2013.01); *A61B 2018/00744* (2013.01); *A61B 2018/00773* (2013.01); *A61B 2018/00863* (2013.01); *A61B 2018/00892* (2013.01); *A61B 2018/00898* (2013.01); *A61B 2018/0212* (2013.01); *A61B 2018/0231* (2013.01); *A61B 2218/007* (2013.01); *A61M 2025/004* (2013.01); *A61M 2025/0034* (2013.01); *A61M 2025/0036* (2013.01)
(58) Field of Classification Search
　　　CPC .. A61M 2025/0034; A61M 2025/0036; A61M 2025/004
　　　USPC ..................................................... 606/21–26
　　　See application file for complete search history.

FLUID DETECTION ASSEMBLY FOR A MEDICAL DEVICE

CROSS-REFERENCE TO RELATED APPLICATION

This application claims priority to Provisional Application No. 62/573,030, filed Oct. 16, 2017, which is herein incorporated by reference in its entirety.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (farthest from the operator) portion of the catheter, and often at the tip of the catheter.

Various forms of energy are used to ablate diseased heart tissue. One form of energy that is used to ablate diseased heart tissue includes cryogenics (also referred to herein as "cryoablation"). During the cryoablation procedure, the tip of the catheter is positioned adjacent to target cardiac tissue, at which time energy is delivered to create tissue necrosis, rendering the ablated tissue incapable of conducting electrical signals.

For medical devices intended for use within the patient's body, such as the catheter, the detection of fluid contamination and/or the type of a fluid such as blood inside the medical device can be significant to identify potential risks to patient health. For example, during cryoablation procedures, the catheter is designed to reach tissue within the patient's heart. In order to reach various locations within the heart, catheter ablation requires that the catheter be carefully steered through the patient's body, particularly the patient's vascular system. If at any point during the cryoablation procedure, blood is detected within the catheter, the health of the patient would be put at significant risk since a cryogenic fluid could be injected or otherwise be expelled into the patient's blood stream.

The detection of fluid contamination within the medical device is generally realized by complex configurations requiring numerous working components. Such complex configurations make it necessary to utilize a greater area in order to include and/or integrate all of the working components. The increased area limits and/or restricts the number of locations where such components can be positioned within the medical device. Further, inclusion and/or integration of the many working components can also increase the likelihood of long term component drift, which can reduce the reliability or stability of such working components over time.

SUMMARY

The present invention is directed toward a fluid detection assembly for detecting fluid contamination within a medical device. In certain embodiments, the fluid detection assembly includes a first pair of detection wires and a controller. In various embodiments, the first pair of detection wires includes an input first detection wire and an output first detection wire that is spaced apart from the input first detection wire. The input first detection wire and the output first detection wire are in fluid communication with one another. The input first detection wire conducts a first electrical signal and the output first detection wire receives the first electrical signal. The controller receives the first electrical signal from the output first detection wire and determines a first propagation delay. The controller determines whether fluid contamination within the medical device has occurred based at least in part on the first propagation delay.

In some embodiments, the controller determines a type of fluid contamination within the medical device based at least in part on the first propagation delay. In certain embodiments, the type of fluid contamination can include blood and/or saline contamination.

In some embodiments, the medical device can include a catheter or a balloon catheter. The balloon catheter can include a vacuum lumen. In various embodiments, at least a portion of the first pair of wires can be positioned within the vacuum lumen.

In certain embodiments, the balloon catheter can include an inner cryoballoon and an outer cryoballoon that define an inter-cryoballoon space between the inner cryoballoon and the outer cryoballoon. In some such embodiments, at least a portion of the first pair of detection wires can be positioned within the inter-cryoballoon space.

In various embodiments, the input first detection wire can include a fluid injection tube that acts as a conduit for cryogenic fluid within the medical device. The fluid injection tube can be formed at least partially from nitinol. In some embodiments, the output first detection wire can be formed from American Wire Gauge 38, or the like. In some embodiments, the output first detection wire can be helically positioned around the input first detection wire.

In certain embodiments, the fluid detection assembly can include a second pair of detection wires that is spaced apart from the first pair of detection wires. In some such embodiments, the second pair of detection wires includes an input second detection wire and an output second detection wire that is spaced apart from the input second detection wire. In certain embodiments, the input second detection wire and the output second detection wire are in fluid communication with one another. The input second detection wire can conduct a second electrical signal and the output second detection wire can receive the second electrical signal. In some embodiments, the controller receives the second electrical signal from the output second detection wire and determines a second propagation delay. The controller can determine whether fluid contamination within the medical device has occurred based at least in part on the second propagation delay.

The present invention is also directed toward a medical device including the fluid detection assembly and a graphical display that is in electrical communication with the fluid detection assembly. The graphical display can alternately display one of a presence and an absence of fluid contamination.

The present invention is also directed toward a method for detecting the fluid contamination within a medical device. In certain embodiments, the method includes the steps of sending a first electrical signal through a first pair of detection wires, including an input first detection wire and an output first detection wire that is spaced apart from the input first detection wire, the input first detection wire and the output first detection wire being in fluid communication with one another, wherein the input first detection wire conducts the first electrical signal and the output first detection wire receives the first electrical signal; receiving the first electrical signal from the first pair of detection wires by a controller; and determining a first propagation delay by the controller, the controller determining whether fluid contamination within the medical device has occurred based at least in part on the first propagation delay.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION

Embodiments of the present invention are described herein in the context of a fluid detection assembly for a medical device. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on medical devices including cryogenic balloon catheters, it is understood that various other forms of energy can be used to ablate heart tissue. These can include radio frequency (RF), ultrasound, pulsed DC electric fields and laser energy, as non-exclusive examples. The present invention is intended to be effective with any or all of these and other forms of energy.

Figure 1:
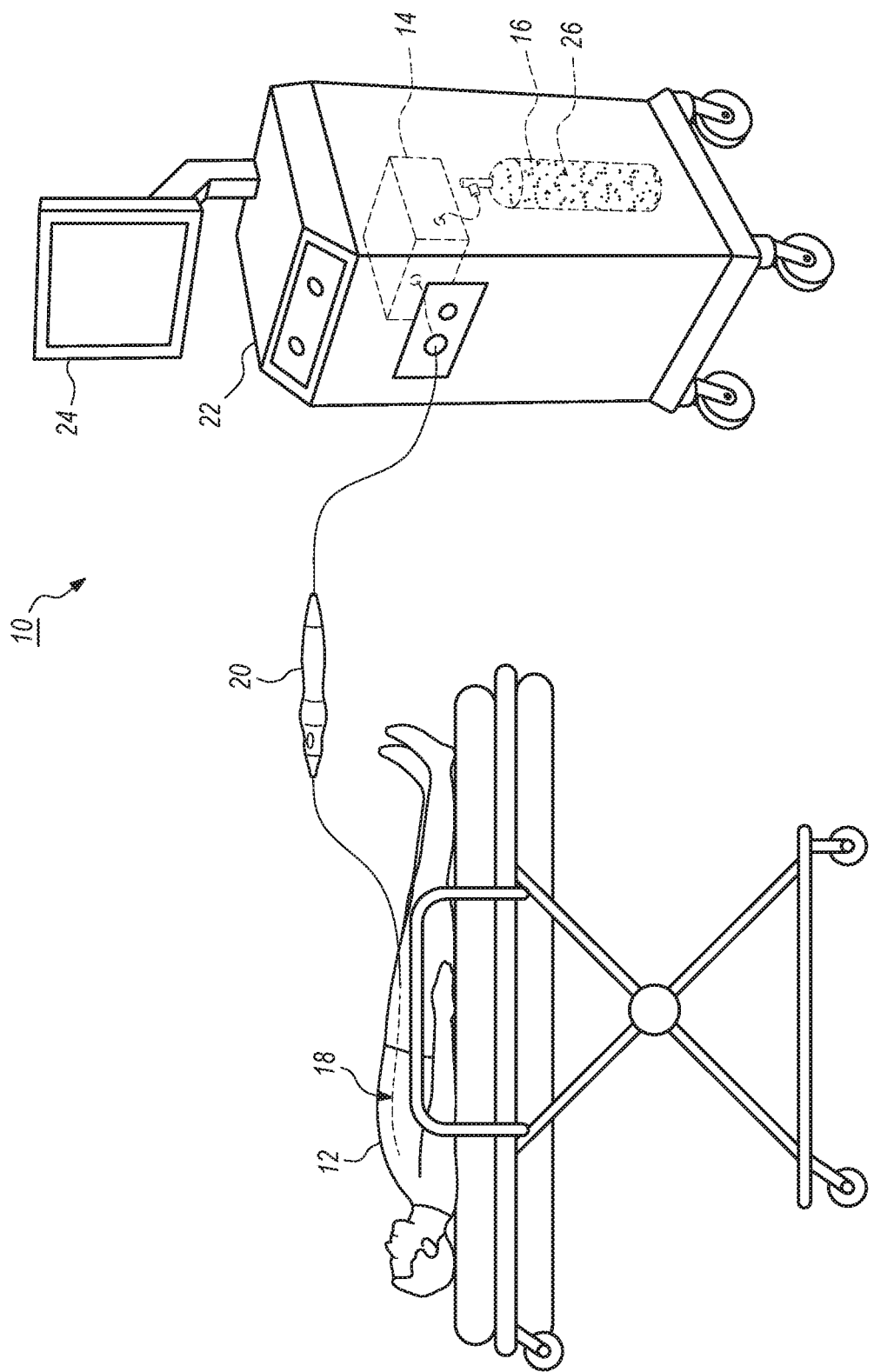
FIG. 1 is a simplified schematic side view illustration of a patient and an embodiment of a medical device having features of the present invention.

FIG. 1 is a schematic side view illustration of one embodiment of a medical device 10 for use with a patient 12, which can be a human being or an animal. Although the specific medical device 10 shown and described herein pertains to and refers to a cryogenic balloon catheter system 10, it is understood and appreciated that other types of medical devices 10 can equally benefit by the teachings provided herein. The design of the cryogenic balloon catheter system 10 can be varied. In certain embodiments such as the embodiment illustrated in FIG. 1, the cryogenic balloon catheter system 10 can include one or more of a control system 14, a fluid source 16, a balloon catheter 18, a handle assembly 20, a control console 22 and a graphical display 24. It is understood that although FIG. 1 illustrates the structures of the cryogenic balloon catheter system 10 in a particular position, sequence and/or order, these structures can be located in any suitably different position, sequence and/or order than that illustrated in FIG. 1.

In various embodiments, the control system 14 can control release and/or retrieval of a cryogenic fluid 26 to and/or from the balloon catheter 18. In various embodiments, the control system 14 can control activation and/or deactivation of one or more other processes of the balloon catheter 18. Additionally, or in the alternative, the control system 14 can receive data and/or other information (hereinafter sometimes referred to as "sensor output") from various structures within the cryogenic balloon catheter system 10. In some embodiments, the control system 14 can assimilate and/or integrate the sensor output, and/or any other data or information received from any structure within the cryogenic balloon catheter system 10. Additionally, or in the alternative, the control system 14 can control positioning of portions of the balloon catheter 18 within the body of the patient 12, and/or can control any other suitable functions of the balloon catheter 18.

The fluid source 16 contains the cryogenic fluid 26, which is delivered to the balloon catheter 18 with or without input from the control system 14 during a cryoablation procedure. The type of cryogenic fluid 26 that is used during the cryoablation procedure can vary. In one non-exclusive embodiment, the cryogenic fluid 26 can include liquid nitrous oxide. However, any other suitable cryogenic fluid 26 can be used.

The balloon catheter 18 is inserted into the body of the patient 12. In one embodiment, the balloon catheter 18 can be positioned within the body of the patient 12 using the control system 14. Alternatively, the balloon catheter 18 can be manually positioned within the body of the patient 12 by a health care professional (also sometimes referred to herein as an "operator"). In certain embodiments, the balloon catheter 18 is positioned within the body of the patient 12 utilizing the sensor output from the balloon catheter 18. In various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12. While specific reference is made herein to the balloon catheter 18, it is understood that any suitable type of medical device and/or catheter may be used.

The handle assembly 20 is handled and used by the operator to operate, position and control the balloon catheter 18. The design and specific features of the handle assembly 20 can vary to suit the design requirements of the cryogenic balloon catheter system 10. In the embodiment illustrated in FIG. 1, the handle assembly 20 is separate from, but in electrical and/or fluid communication with the control system 14, the fluid source 16 and/or the graphical display 24. In some embodiments, the handle assembly 20 can integrate and/or include at least a portion of the control system 14 within an interior of the handle assembly 20. It is understood that the handle assembly 20 can include fewer or additional components than those specifically illustrated and described herein.

In the embodiment illustrated in FIG. 1, the control console 22 includes the control system 14, the fluid source 16 and the graphical display 24. However, in alternative embodiments, the control console 22 can contain additional structures not shown or described herein. Still alternatively, the control console 22 may not include various structures that are illustrated within the control console 22 in FIG. 1. For example, in one embodiment, the control console 22 does not include the graphical display 24.

The graphical display 24 provides the operator of the cryogenic balloon catheter system 10 with information that can be used before, during and after the cryoablation procedure. The specifics of the graphical display 24 can vary depending upon the design requirements of the cryogenic balloon catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time. Further, in various embodiments, the graphical display 24 can include one or more colors, different sizes, varying brightness, etc., that may act as alerts to the operator. Additionally, or in the alternative, the graphical display can provide audio data or information to the operator.

Figure 2A:
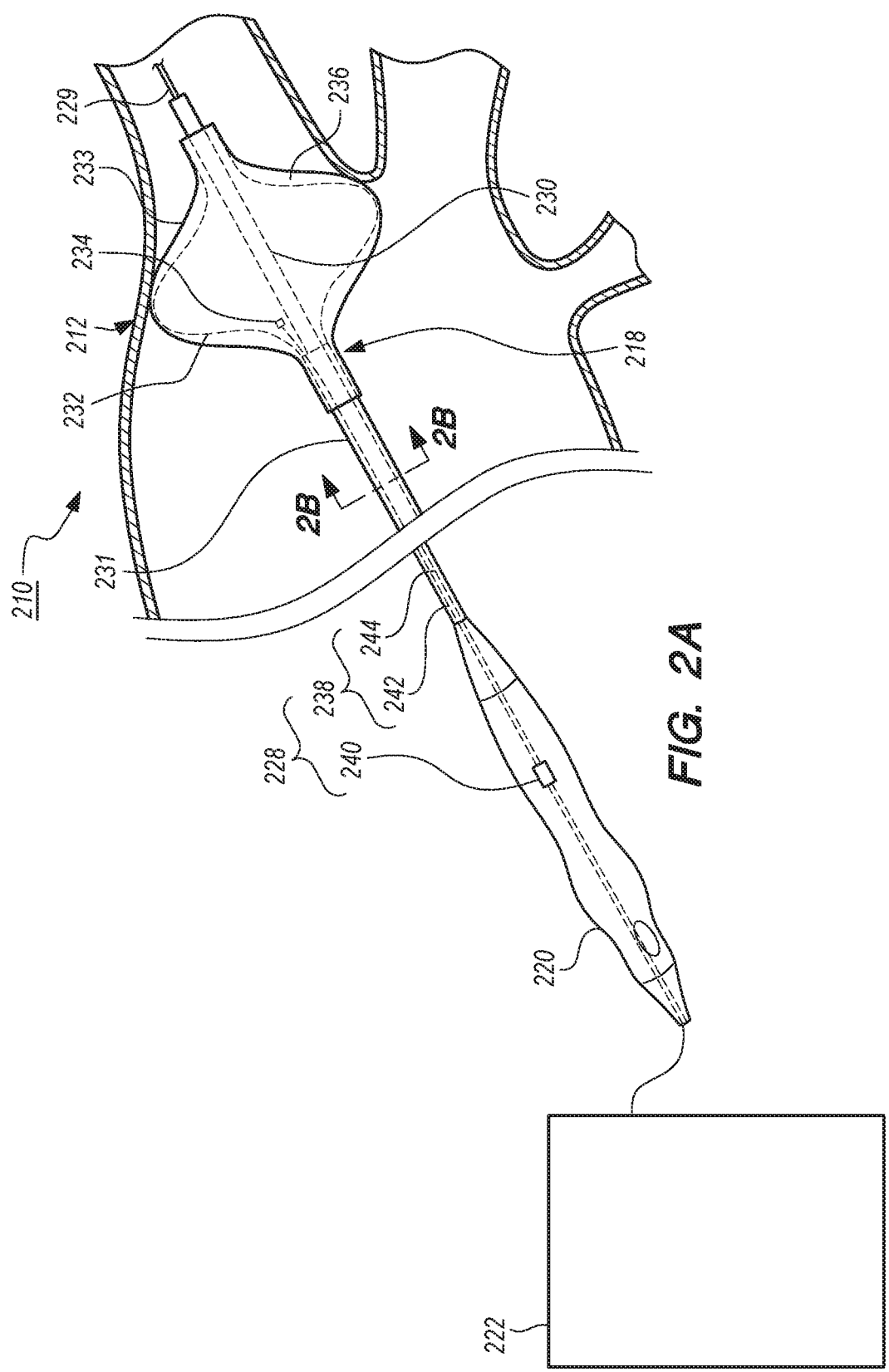
FIG. 2A is a simplified schematic side view illustration of a portion of the patient and one embodiment of a portion of the medical device including an embodiment of a fluid detection assembly.

FIG. 2A is a simplified schematic side view illustration of a portion of the patient 212 and one embodiment of a portion of the medical device 210, such as the cryogenic balloon catheter system 210. In the embodiment illustrated in FIG. 2A, the cryogenic balloon catheter system 210 can include one or more of the balloon catheter 218, the handle assembly 220, the control console 222 and a fluid detection assembly 228.

The balloon catheter 218 is inserted into the body of the patient 212 during the cryoablation procedure. The design of the balloon catheter 218 can be varied to suit the specific design requirements of the cryogenic balloon catheter system 210. In the embodiment illustrated in FIG. 2A, the balloon catheter 218 includes a guidewire 229, a guidewire lumen 230, a catheter shaft 231, an inner cryoballoon 232, an outer cryoballoon 233 and a sniffer tube 234.

The guidewire 229 and guidewire lumen 230 are inserted into the patient 212, and the catheter shaft 231 and the cryoballoons 232, 233, are moved along the guidewire 229 and/or guidewire lumen 230 to a desired location within the patient 212. The outer cryoballoon 233 substantially encircles and/or surrounds the inner cryoballoon 232. Together, the inner cryoballoon 232 and the outer cryoballoon 233 define an inter-cryoballoon space 236 between the inner cryoballoon 232 and the outer cryoballoon 233. The sniffer tube 234 is in fluid communication with the inter-cryoballoon space 236. In such embodiments, the sniffer tube 234 can include a relatively small diameter tube that can extend through portions of the balloon catheter 218 to the inter-cryoballoon space 236. It is understood that the balloon catheter 218 can include other structures as well that are not shown and/or described relative to FIG. 2A.

In the embodiment illustrated in FIG. 2A, the control console 222 can be substantially similar or the same as the control console 22 (illustrated in FIG. 1) previous described herein. It is further understood that the control console 222 can include additional components than those specifically illustrated and described herein.

The fluid detection assembly 228 detects fluid contamination and/or the type of fluid within the cryogenic balloon catheter system 210 during cryoablation procedures. In certain embodiments, the fluid contamination can include blood contamination. In other embodiments, the fluid contamination can include saline contamination. Further, in certain embodiments the fluid can include blood. In other embodiments, the fluid can include a gas, or another liquid such as saline, as one non-exclusive example. Alternatively, the fluid detection assembly 228 can detect any type of fluid contamination and/or the presence of any other type of fluid.

The design of the fluid detection assembly 228 can vary. In the embodiment illustrated in FIG. 2A, the fluid detection assembly 228 includes a first pair of detection wires 238 and a controller 240. It is understood that the fluid detection assembly 228 can include additional components other than those specifically illustrated and described herein. While specific reference is made herein to the cryogenic balloon catheter system 210, particularly the balloon catheter 218, as it relates to the fluid detection assembly 228, it is understood that any suitable type of medical device 210 and/or catheter can include and/or integrate the fluid detection assembly 228 during any type of procedure that is to be performed within the body of the patient 212.

The first pair of detection wires 238 can conduct, transmit and/or receive an electrical signal (as described in more detail below). The electrical signal can be generated from any suitable source within or outside of the cryogenic balloon catheter system 210. The electrical signal can be a digital signal, for example. Alternatively, the electrical signal can be of any other suitable type of signal.

In certain embodiments, the first pair of detection wires 238 can include an input first detection wire 242 and an output first detection wire 244 that is spaced apart from the input first detection wire 242. In some embodiments, the input first detection wire 242 can conduct the electrical signal and the output first detection wire 244 can receive the electrical signal from the input first detection wire 242. The electrical signal that is conducted by the input first detection wire 242 is also sometimes referred to herein as the "first electrical signal". During cryoablation procedures, the input first detection wire 242 and the output first detection wire 244 can be in fluid communication with one another. For example, during such procedures, the input first detection wire 242 and the output first detection wire 244 can come into contact with any fluid, such as air, nitrous oxide, blood, saline or any other fluid that may be present.

In the embodiment illustrated in FIG. 2A, the first pair of detection wires 238 can be connected to and/or can extend from the handle assembly 220. In alternative embodiments, the first pair of detection wires 238 can be connected to and/or can extend from or through other structures and/or components of the cryogenic balloon catheter system 210. While the embodiment illustrated in FIG. 2A only shows the first pair of detection wires 238, it is understood that the fluid detection assembly 228 can include a greater number of pairs of detection wires 238. In various embodiments, portions of the first pair of detection wires 238 can be positioned in any suitable location within the balloon catheter 218. For example, as illustrated in FIG. 2A, portions of the first pair of detection wires 238 can be positioned at least partially within the sniffer tube 234. Stated another way, the sniffer tube 234 can act as a conduit for the first pair of detection wires 238. In some embodiments, the first pair of detection wires 238 can extend through and to the outside of the sniffer tube and into the inter-cryoballoon space 236. In other embodiments, the first pair of detection wires 238 can stop short of the outside of the sniffer tube 234. Additionally, or in the alternative, the sniffer tube 234 can have different functions within the cryogenic balloon catheter system 210. It is understood that the first pair of detection wires 238 can alternatively, or additionally, be positioned at any other suitable location or within any other suitable structure and/or component of the cryogenic balloon catheter system 210.

The controller 240 is configured to generate the electrical signal to be sent to the first pair of detection wires 238 and/or to receive and process the electrical signal from the first pair of detection wires 238. The design of the controller 240 can vary. In various embodiments, the controller 240 can generate and/or initiate the electrical signal as a single pulse. In other embodiments, the electrical signal can be generated and/or initiated as a series of pulses. In certain embodiments, the pulse or series of pulses can be initiated by the occurrence of an event during a medical procedure. Still alternatively, the pulse or series of pulses can be initiated at predetermined intervals and/or at random times.

In various embodiments, the controller 240 can process the electrical signal to determine fluid contamination and/or detect the type of fluid. The controller 240 can process the electrical signal to determine fluid contamination and/or detect the type of fluid by using any one or more of various problem-solving operations, which can include an algorithm, interpolation and/or extrapolation, as non-exclusive examples. Alternatively, the controller 240 can process the electrical signal to determine fluid contamination and/or detect the type of the fluid via any other suitable method. Further, in the embodiment illustrated in FIG. 2A, the controller 240 can be included as part of the handle assembly 220. In other embodiments, the controller 240 can be separate from the handle assembly 220. Still in other embodiments, the controller 240 can be included as part of the control system 14 (illustrated in FIG. 1).

Figure 2B:
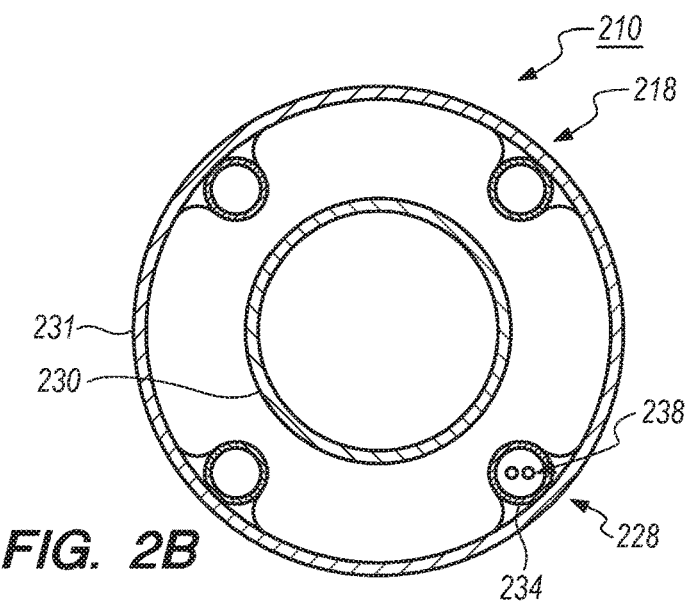
FIG. 2B is a simplified cross-sectional view of a portion of the medical device taken on line 2B-2B in FIG. 2A.

FIG. 2B is a simplified cross-sectional view of a portion of the medical device 210 including a portion of the fluid detection assembly 228 taken on line 2B-2B in FIG. 2A. In the embodiment illustrated in FIG. 2B, the fluid detection assembly 228 includes the first pair of detection wires 238, which are positioned within the balloon catheter 218, in one non-exclusive example. More specifically, in this embodiment, at least a portion of the first pair of detection wires 238 are positioned within the sniffer tube 234, which can be positioned between the guidewire lumen 230 and the catheter shaft 231. In alternative embodiments, the first pair of detection wires 238 can be positioned at any location and/or within any structure of the cryogenic balloon catheter system 210. In certain embodiments, the first pair of detection wires 238 may be formed from any suitable electrically conducting material(s). For ease of understanding, only certain components have been illustrated in the embodiment illustrated in FIG. 2B. However, it is understood that the balloon catheter 218 can include additional components other than those specifically illustrated and described relative to FIG. 2B.

Figure 2C:
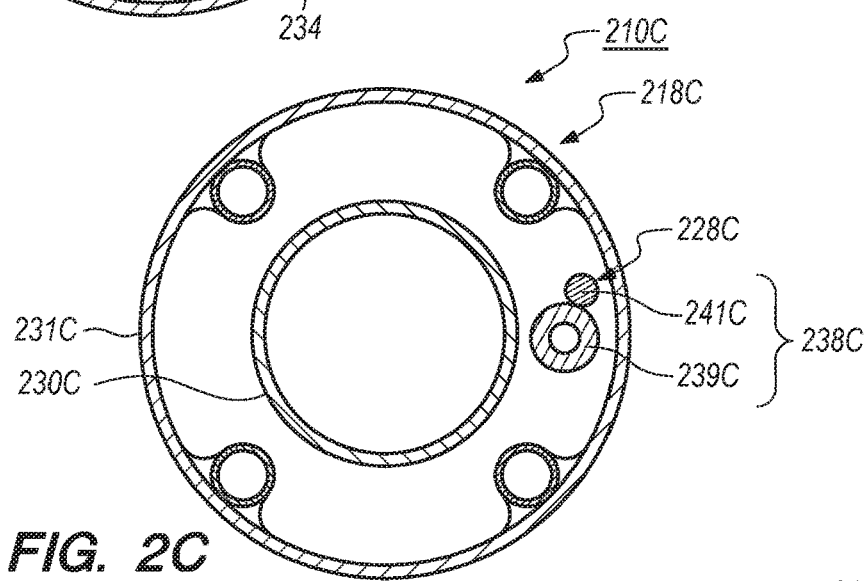
FIG. 2C is a simplified cross-sectional view of another embodiment of a portion of the medical device in FIG. 2A.

FIG. 2C is a simplified cross-sectional view of another embodiment of a portion of the medical device 210C including a portion of the fluid detection assembly 228 illustrated in FIG. 2A. In the embodiment illustrated in FIG. 2C, the fluid detection assembly 228C includes the first pair of detection wires 238C, which are positioned within the balloon catheter 218C, in one non-exclusive example. More specifically, in this embodiment, at least a portion of the first pair of detection wires 238C are positioned in a vacuum lumen 252C, which can be positioned between the guidewire lumen 230C and the catheter shaft 231C. In alternative embodiments, the first pair of detection wires 238C can be positioned at any location and/or within any other suitable structure of the cryogenic balloon catheter system 210C. For ease of understanding, only certain components have been illustrated in the embodiment illustrated in FIG. 2C. However, it is understood that the balloon catheter 218C can include additional components other than those specifically illustrated and described relative to FIG. 2C.

The first pair of detection wires 238C includes an input first detection wire 242C and an output first detection wire 244C. In the embodiment illustrated in FIG. 2C, the input first detection wire 242C includes a fluid injection tube that acts as a conduit for cryogenic fluid 26 (illustrated in FIG. 1) or another suitable fluid during an ablation procedure. In one such embodiment, the input first detection wire 242C can be formed at least partially from nitinol, for example. The output first detection wire 244C can be formed from any suitably conductive material. For example, in one non-exclusive embodiment, the output first detection wire 244C can include an American Wire Gauge 38 (AWG 38) wire (or another suitable gauge wire).

In the embodiment illustrated in FIG. 2C, the output first detection wire 244C can run substantially along a length of the input first detection wire 242C. Alternatively, the output first detection wire 244C can be helically or spirally wrapped around the input first detection wire 242C. Still alternatively, the output first detection wire 244C can be positioned in another suitable manner relative to the input first detection wire 242C. In this embodiment, the first pair of detection wires 238C can operate in a somewhat similar manner as the first pair of detection wires 238 illustrated and described relative to FIGS. 2A and 2B.

Figure 3A:
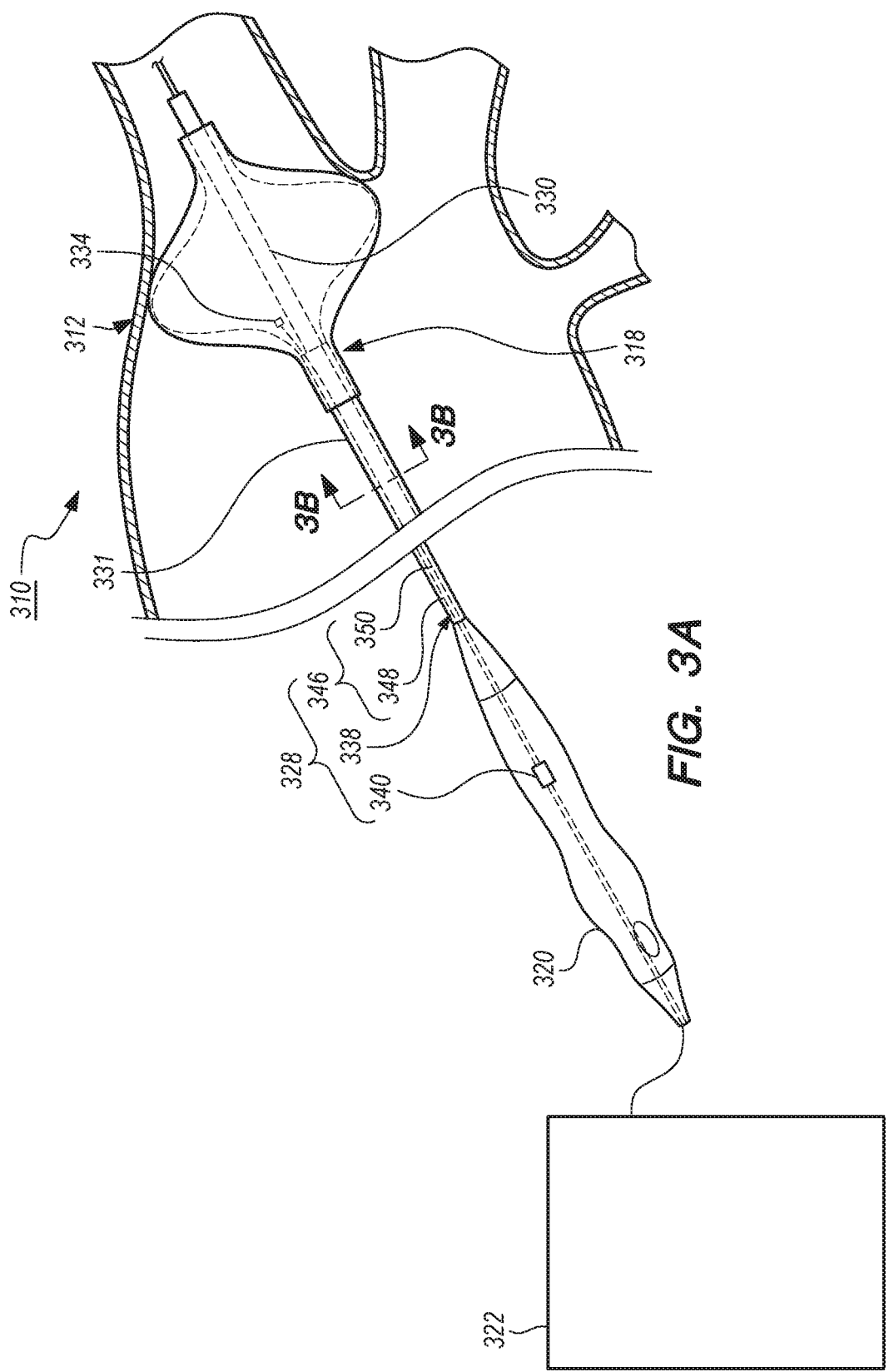
FIG. 3A is a simplified schematic side view illustration of a portion of the patient and another embodiment of a portion of the medical device including an embodiment of the fluid detection assembly.

FIG. 3A is a simplified schematic side view illustration of the patient 312 and an embodiment of a portion of the medical device 310, such as the cryogenic balloon catheter system 310. In the embodiment illustrated in FIG. 3A, the cryogenic balloon catheter system 310 can include one or more of the balloon catheter 318, the handle assembly 320, the control console 322, the fluid detection assembly 328, the guidewire lumen 330 and the catheter shaft 331. In the embodiment illustrated in FIG. 3A, the balloon catheter includes a sniffer tube 334.

In the embodiment illustrated in FIG. 3A, the fluid detection assembly 328 includes the first pair of detection wires 338 that operate in a substantially similar manner as the first pair of detection wires 238 described and illustrated with respect to FIG. 2A, and the controller 340. However, in this embodiment, the fluid detection assembly 328 can also include a second pair of detection wires 346 positioned within the balloon catheter 318. In certain embodiments, the second pair of detection wires 346 can include an input second detection wire 348 and an output second detection wire 350 that is spaced apart from the input second detection wire 348. The second pair of detection wires 346 can operate in a substantially similar manner as the first pair of detection wires 338. As used herein, the terms "first pair of detection wires" and "second pair of detection wires" can be used interchangeably. Stated another way, either pair of detection wires can be the first pair of detection wires or the second pair of detection wires.

In some embodiments, the input second detection wire 348 can conduct a second electrical signal and the output second detection wire 350 can receive the second electrical signal from the input second detection wire 348. During cryoablation procedures, the input second detection wire 348 and the output second detection wire 350 can be in fluid communication with one another. For example, during such procedures, the input second detection wire 348 and the output second detection wire 350 can come into contact with any fluid, such as air, nitrous oxide, blood, saline or any other fluid that may be present.

In the embodiment illustrated in FIG. 3A, the second pair of detection wires 346 can be connected to and extend from the handle assembly 320. In alternative embodiments, the second pair of detection wires 346 can be connected to and/or extend through other structures and/or components of the cryogenic balloon catheter system 310. In various embodiments, portions of the second pair of detection wires 346 can be positioned in any suitable location within the balloon catheter 318.

Figure 3B:
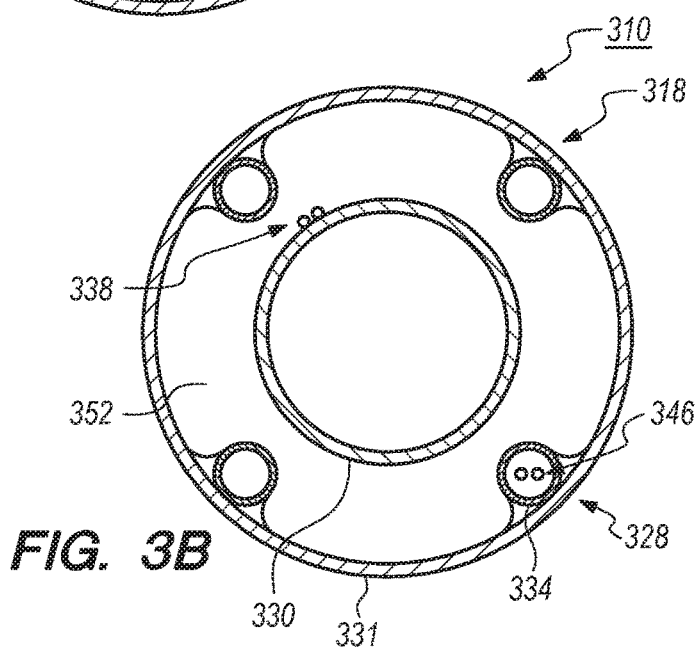
FIG. 3B is a simplified cross-sectional view of a portion of the medical device taken on line 3B-3B in FIG. 3A.

FIG. 3B is a simplified cross-sectional view of a portion of the medical device 310 including a portion of the fluid detection assembly 328 taken on line 3B-3B in FIG. 3A. In the embodiment illustrated in FIG. 3B, the fluid detection assembly 328 includes the first pair of detection wires 338 and the second pair of detection wires 346, which are positioned within the balloon catheter 318. More specifically, in this embodiment, portions of the second pair of detection wires 346 can be positioned within the sniffer tube 334 and portions of the first pair of detection wires 338 can be positioned within a vacuum lumen 352 that is positioned between the guidewire lumen 330 and the catheter shaft 331, in one non-exclusive embodiment. The vacuum lumen 352 can function as a conduit through which cryogenic fluid 26 (illustrated in FIG. 1), typically in gas form, can be removed as exhaust from the balloon catheter 318. Additionally, or in the alternative, the vacuum lumen 352 can have different functions within the cryogenic balloon catheter system 310. In alternative embodiments, the first pair of detection wires 338 and/or the second pair of detection wires 346 can be positioned at any suitable location and/or within any suitable structure of the cryogenic balloon catheter system 310. Further, the first pair of detection wires 338 and/or the second pair of detection wires 346 may be formed from any suitable material(s).

Figure 4A:
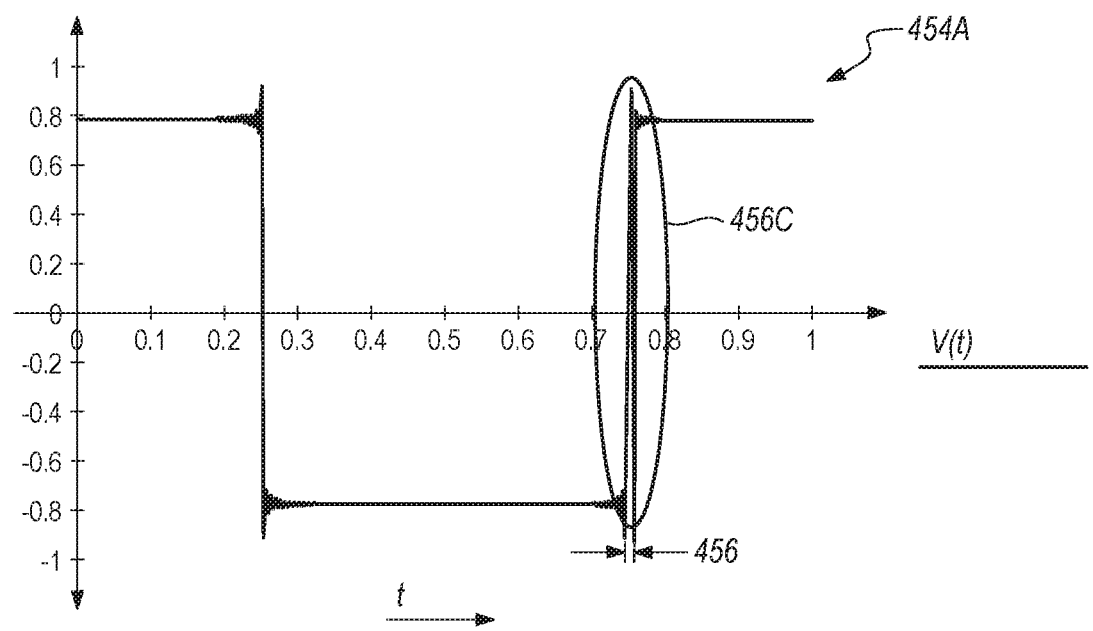
FIG. 4A is a graph showing an electrical signal within the medical device as a function of time.

FIG. 4A is a graph showing an electrical signal 454A (also illustrated in FIG. 4A as V(t)) within the medical device 210, 310 (illustrated in FIGS. 2A and 3A, respectively) as a function of time, wherein:

$$V(t) := \sum_n \left( \left( \frac{1}{n} \cos((n)w \cdot t) \right) - \frac{1}{(n+2)} \cos((n+2)w \cdot t) \right).$$

The electrical signal 454A can include a first propagation delay 456, illustrated in oval 456C. The first propagation delay 456 can include an interval of time for the electrical signal 454A to transition from a peak negative voltage to a peak positive voltage, and vice versa. The first propagation delay 456 can vary for different reasons including the extent of fluid contamination and/or the type of the fluid within the medical device 210, 310, as non-exclusive examples.

During operation, in certain embodiments, the controller 240, 340 (illustrated in FIGS. 2A and 3A) can receive the electrical signal 454A from one of the pairs of detection wires 238, 338, 346 (illustrated in FIGS. 2A, 2B, 3A and 3B), i.e., the output detection wires 244, 350 (illustrated in FIGS. 2A and 3A), and can process and/or determine the first propagation delay 456. In such embodiments, the controller 240, 340 can determine fluid contamination and/or detect the type of the fluid, such as blood, within the medical device 210, 310 based at least in part on the first propagation delay 456.

In certain embodiments, such as the embodiment illustrated in FIG. 4A, the first propagation delay 456 can include a relatively short interval of time. In such embodiments, the electrical signal 454A can form a somewhat square wave pattern as the electrical signal 454A transitions from the peak negative voltage to the peak positive voltage, and vice versa. In FIG. 4A, due to the relatively short duration of the first propagation delay 456, the controller 240, 340 can process and/or determine that there is no fluid contamination, such as blood, within the medical device 210, 310.

Figure 4B:
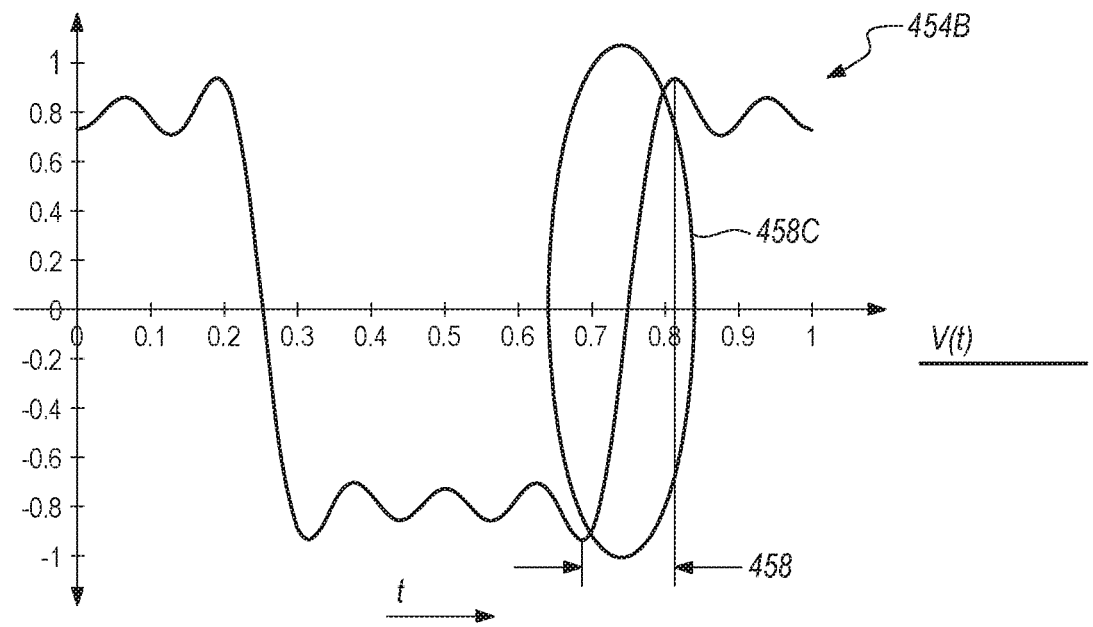
FIG. 4B is a graph showing another electrical signal within the medical device as a function of time.

FIG. 4B is a graph showing another electrical signal 454B (also illustrated in FIG. 4B as V(t)) within the medical device 210, 310 (illustrated in FIGS. 2A and 3A, respectively) as a function of time, wherein:

$$V(t) := \sum_n \left( \left( \frac{1}{n} \cos((n)w \cdot t) \right) - \frac{1}{(n+2)} \cos((n+2)w \cdot t) \right).$$

In the embodiment illustrated in FIG. 4B, the electrical signal 454B can include a second propagation delay 458, illustrated in oval 458C. The second propagation delay 458 includes the interval of time for the electrical signal 454B to transition from a peak negative voltage to a peak positive voltage, and vice versa. The second propagation delay 458 can vary due to fluid contamination and/or the type of the fluid within the medical device 210, 310, as non-exclusive examples.

During operation, in certain embodiments, the controller 240, 340 (illustrated in FIGS. 2A and 3A, respectively) can receive the electrical signal 454B from one of the pair of detection wires 238, 338, 346 (illustrated in FIGS. 2A, 2B, 3A and 3B), i.e., the output detection wires 244, 350 (illustrated in FIGS. 2A and 3A), and can process and/or determine the second propagation delay 458. In such embodiments, the controller 240, 340 can determine fluid contamination and/or detect the type of the fluid, such as blood, within the medical device 210, 310 based at least in part on the relatively long duration of the second propagation delay 458.

In FIG. 4B, the second propagation delay 458 is greater than the first propagation delay 456 (illustrated in FIG. 4A). In other words, the second propagation delay 458 has deviated from and has a longer duration than the first propagation delay 456. Further, in FIG. 4B, the wave pattern of the electrical signal 454B has become less square and/or somewhat more distorted than the wave pattern of the electrical signal 454A illustrated in FIG. 4A as the electrical signal 454B transitions from the peak negative voltage to the peak positive voltage, and vice versa. In the embodiment illustrated in FIG. 4B, due to an increase and/or deviation of the duration of the second propagation delay 458 relative to the duration of the first propagation delay 456, the controller 240, 340 can process and/or determine that there is or has been fluid contamination, such as by blood, within the medical device 210, 310.

In various embodiments, the controller 240, 340 can determine whether there is fluid contamination and/or detect the type of the fluid within the medical device 210, 310 by processing and/or determining whether the second propagation delay 458 has deviated from the first propagation delay 456. For example, in one embodiment, the controller 240, 340 can determine fluid contamination and/or detect the type of the fluid if the duration of the second propagation delay 458 increases and/or deviates by at least approximately 1% from the duration of the first propagation delay. In other non-exclusive alternative embodiments, the controller 240, 340 can determine fluid contamination and/or detect the type of the fluid if the duration of the second propagation delay 458 increases and/or deviates by at least approximately 2%, 5%, 10%, 25, %, 50%, 100%, 500%, 1,000% or some other percentage from the duration of the first propagation delay 456. Still alternatively, any other suitable percentage deviation and/or difference can be utilized.

Figure 4C:
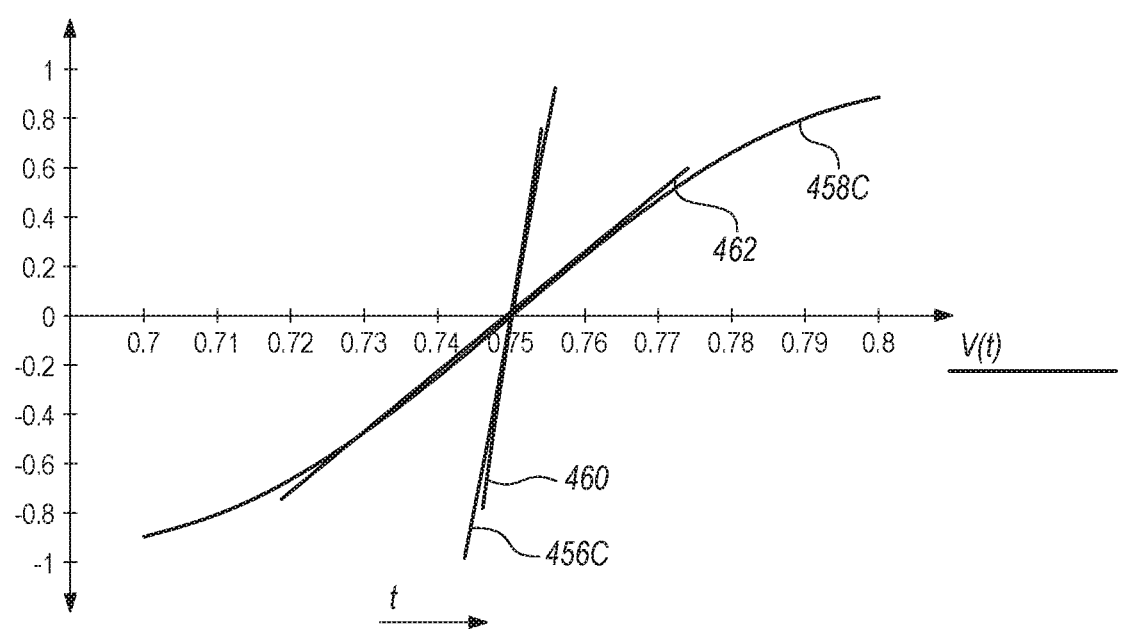
FIG. 4C is a graph showing a close-up of portions of the graphs in FIGS. 4A and 4B.

FIG. 4C is a graph showing a close-up of portions of the graphs illustrated in FIGS. 4A and 4B. In particular, FIG. 4C illustrates close-up portions of the graphs in oval 456C in FIG. 4A and oval 458C in FIG. 4B. In FIG. 4C, the electrical signal 454A can include a first propagation slope 460 and the electrical signal 454B can include a second propagation slope 462. The propagation slopes 460, 462 can be a function of the electrical signals 454A, 454B and/or the propagation delays 456, 458 (illustrated in FIGS. 4A and 4B). The propagation slopes 460, 462 can vary due to the degree of fluid contamination and/or the type of the fluid within the medical device 210, 310 (illustrated in FIGS. 2A and 3A).

In certain embodiments, the controller 240, 340 (illustrated in FIGS. 2A and 3A) can determine whether there is fluid contamination and/or the type of the fluid within the medical device 210, 310 by processing and/or determining whether the second propagation slope 462 has deviated and/or decreased from the first propagation slope 460. For example, in one embodiment, the controller 240, 340 can determine fluid contamination and/or detect the type of the fluid if the second propagation slope 462 decreases and/or deviates by at least approximately 1% from the first propagation slope 460. In other non-exclusive alternative embodiments, the controller 240, 340 can determine fluid contamination and/or detect the type of the fluid if the second propagation slope 462 decreases and/or deviates by at least approximately 5%, 10%, 25%, 50%, 100%, or some other greater percentage from the first propagation slope 460, as non-exclusive examples. Still alternatively, any other suitable percentage deviation and/or difference can be utilized.

It is appreciated that the embodiments of the fluid detection assembly described in detail herein enable the realization of one or more certain advantages during the cryoablation procedure. With the various designs illustrated and described herein, the fluid detection assembly can include a relatively simple configuration that can allow the fluid detection assembly to be positioned and/or integrated in substantially more locations. In addition, the fluid detection assembly can improve flexibility of the balloon catheter by allowing the detection process to be suspended, continuous and/or synchronized with other functions. The fluid detection assembly can also substantially reduce the effect of component drift which can provide a more reliable or stable detection process over time. Further, the fluid detection assembly can substantially reduce the susceptibility to electrical noise, making the fluid detection assembly more ideal for noisy environments.

It is understood that although a number of different embodiments of the fluid detection assembly have been illustrated and described herein, one or more features of any one embodiment can be combined with one or more features of one or more of the other embodiments, provided that such combination satisfies the intent of the present invention.

While a number of exemplary aspects and embodiments of the fluid detection assembly have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

I claim:

1. A fluid detection assembly for detecting fluid contamination within a medical device, the fluid detection assembly comprising:
 a first pair of detection wires, including an input first detection wire and an output first detection wire that is spaced apart from the input first detection wire, the input first detection wire and the output first detection wire being in fluid communication with one another, wherein the input first detection wire conducts a first electrical signal and the output first detection wire receives the first electrical signal; and
 a controller that receives the first electrical signal from the output first detection wire and determines a first propagation delay including an interval of time for the first electrical signal to transition from a peak negative voltage to a peak positive voltage or vice versa, the controller determining whether fluid contamination within the medical device has occurred based at least in part on the first propagation delay.

2. The fluid detection assembly of claim 1, wherein the controller determines a type of fluid contamination within the medical device based at least in part on the first propagation delay.

3. The fluid detection assembly of claim 1 wherein the medical device includes a balloon catheter having a vacuum lumen, and wherein at least a portion of the first pair of wires is positioned within the vacuum lumen.

4. The fluid detection assembly of claim 1, wherein the medical device includes a balloon catheter having an inner cryoballoon and an outer cryoballoon that define an inter-cryoballoon space between the inner cryoballoon and the outer cryoballoon, and at least a portion of the first pair of detection wires is positioned within the inter-cryoballoon space.

5. The fluid detection assembly of claim 1, wherein the input first detection wire includes a fluid injection tube that acts as a conduit for cryogenic fluid within the medical device.

6. The fluid detection assembly of claim 5, wherein the output first detection wire is helically positioned around the input first detection wire.

7. The fluid detection assembly of claim 1, further comprising a second pair of detection wires that is spaced apart from the first pair of detection wires, the second pair of detection wires including an input second detection wire and an output second detection wire that is spaced apart from the input second detection wire, the input second detection wire and the output second detection wire being in fluid communication with one another, wherein the input second detection wire conducts a second electrical signal and the output second detection wire receives the second electrical signal.

8. The fluid detection assembly of claim 7, wherein the controller receives the second electrical signal from the output second detection wire and determines a second propagation delay including an interval of time for the second electrical signal to transition from a peak negative voltage to a peak positive voltage or vice versa, the controller determining whether fluid contamination within the medical device has occurred based at least in part on the second propagation delay.

9. A medical device comprising:
   a fluid detection assembly comprising:
      a first pair of detection wires, including an input first detection wire and an output first detection wire that is spaced apart from the input first detection wire, the input first detection wire and the output first detection wire being in fluid communication with one another, wherein the input first detection wire conducts a first electrical signal and the output first detection wire receives the first electrical signal; and
      a controller that receives the first electrical signal from the output first detection wire and determines a first propagation delay including an interval of time for the first electrical signal to transition from a peak negative voltage to a peak positive voltage or vice versa, the controller determining whether fluid contamination within the medical device has occurred based at least in part on the first propagation delay; and
      a graphical display that is in electrical communication with the fluid detection assembly, the graphical display alternately displaying one of a presence and an absence of fluid contamination.

10. The medical device of claim 9, wherein the controller determines a type of fluid contamination within the medical device based at least in part on the first propagation delay.

11. The medical device of claim 9, wherein the medical device includes a balloon catheter having a vacuum lumen, and wherein at least a portion of the first pair of wires is positioned within the vacuum lumen.

12. The medical device of claim 9, wherein the medical device includes a balloon catheter having an inner cryoballoon and an outer cryoballoon that define an inter-cryoballoon space between the inner cryoballoon and the outer cryoballoon, and at least a portion of the first pair of detection wires is positioned within the inter-cryoballoon space.

13. The medical device of claim 9, further comprising a second pair of detection wires that is spaced apart from the first pair of detection wires, the second pair of detection wires including an input second detection wire and an output second detection wire that is spaced apart from the input second detection wire, the input second detection wire and the output second detection wire being in fluid communication with one another, wherein the input second detection wire conducts a second electrical signal and the output second detection wire receives the second electrical signal, wherein the controller receives the second electrical signal from the output second detection wire and determines a second propagation delay including an interval of time for the second electrical signal to transition from a peak negative voltage to a peak positive voltage or vice versa, the controller determining whether fluid contamination within the medical device has occurred based at least in part on the second propagation delay.

14. A method for detecting the fluid contamination within a medical device, the method comprising:
   sending a first electrical signal through a first pair of detection wires, including an input first detection wire and an output first detection wire that is spaced apart from the input first detection wire, the input first detection wire and the output first detection wire being in fluid communication with one another, wherein the input first detection wire conducts the first electrical signal and the output first detection wire receives the first electrical signal;
   receiving the first electrical signal from the first pair of detection wires by a controller; and
   determining a first propagation delay including an interval of time for the first electrical signal to transition from a peak negative voltage to a peak positive voltage or vice versa by the controller, the controller determining whether fluid contamination within the medical device has occurred based at least in part on the first propagation delay.

15. The method of claim 14 wherein determining the first propagation delay includes detecting a type of fluid contamination within the medical device based at least in part on the first propagation delay.

16. The method of claim 14 wherein the medical device includes a balloon catheter having a vacuum lumen, and wherein at least a portion of the first pair of detection wires is positioned within the vacuum lumen.

17. The method of claim 14 wherein the medical device includes a balloon catheter having an inner cryoballoon and an outer cryoballoon that define an inter-cryoballoon space between the inner cryoballoon and the outer cryoballoon, and at least a portion of the first pair of detection wires is positioned within the inter-cryoballoon space.

18. The method of claim 14 further comprising:
   sending a second electrical signal through a second pair of detection wires, including an input second detection wire and an output second detection wire that is spaced apart from the input second detection wire, the input second detection wire and the output second detection wire being in fluid communication with one another, wherein the input second detection wire conducts the second electrical signal and the output second detection wire receives the second electrical signal; and
   receiving the second electrical signal from the second pair of detection wires by the controller.

19. The method of claim 18 further comprising determining a second propagation delay including an interval of time for the second electrical signal to transition from a peak negative voltage to a peak positive voltage or vice versa by the controller, the controller determining whether fluid contamination within the medical device has occurred based at least in part on the second propagation delay.

20. The method of claim 19 further comprising detecting a type of fluid contamination within the medical device based at least in part on the second propagation delay.

* * * * *